United States Patent

Radovich et al.

[11] Patent Number: 5,645,778
[45] Date of Patent: Jul. 8, 1997

[54] PROCESS OF MAKING A CELLULOSE ACETATE SEMIPERMEABLE MEMBRANE

[75] Inventors: John M. Radovich, Ft. Lauderdale; Melvin Rothberg, Plantation; George Washington, Miramar, all of Fla.

[73] Assignee: Althin Medical, Inc., Del.

[21] Appl. No.: 456,345

[22] Filed: Jun. 1, 1995

Related U.S. Application Data

[63] Continuation-in-part of Ser. No. 327,431, Oct. 21, 1994, which is a continuation of Ser. No. 976,949, Nov. 16, 1992, abandoned.

[51] Int. Cl.$^6$ ............... B29C 67/20; D01D 5/247
[52] U.S. Cl. ............ 264/41; 264/148; 264/203; 264/211.13; 264/211.14; 264/211.16; 264/211.19; 264/232; 264/233; 264/261
[58] Field of Search ............... 264/41, 148, 200, 264/203, 211.13, 211.14, 211.16, 211.19, 232, 233, 261; 156/77, 242, 245

[56] References Cited

U.S. PATENT DOCUMENTS 4,276,173  6/1981  Kell et al. ............... 264/41 X
4,543,221  9/1985  Chen et al. ............... 264/41
5,182,868  2/1993  Porta et al. ............... 34/18

*Primary Examiner*—Leo B. Tentoni
*Attorney, Agent, or Firm*—Klarquist Sparkman Campbell Leigh & Whinston, LLP

[57] ABSTRACT

Methods are disclosed for making semipermeable membranes from cellulose acetate and for making medical devices therefrom. In the process, a molten liquid comprising cellulose acetate (CA), a solvent for CA, and a non-solvent for CA is extruded to produce a membrane. The solvent and non-solvent are removed from the membrane to produce a semipermeable membrane having a water permeability. The semipermeable membrane is impregnated with a liquid consisting essentially of water to render the semipermeable membrane capable of being stored until time of use without undergoing a substantial loss in water permeability. The semipermeable membrane can be incorporated in a casing in order to produce a medical product, wherein the membrane is impregnated in the product.

10 Claims, 1 Drawing Sheet

PROCESS OF MAKING A CELLULOSE ACETATE SEMIPERMEABLE MEMBRANE

CROSS REFERENCE TO RELATED APPLICATION

This application is a continuation-in-part of U.S. patent application Ser. No. 08/327,431, filed on Oct. 21, 1994, which is a continuation of U.S. patent application Ser. No. 07/976,949, filed on Nov. 16, 1992, now abandoned.

FIELD OF THE INVENTION

This invention pertains to semipermeable membranes, particularly such membranes as used for purifying biological fluids such as blood, as well as medical devices comprising such membranes.

BACKGROUND OF THE INVENTION

Conventional methods for manufacturing cellulose acetate membranes and hollow fibers suitable for medical use include a step in which the membranes are impregnated with an aqueous solution comprising a substantial concentration of glycerin (also termed "glycerol") to maintain hydration of the cellulose acetate until time for their intended use. Because glycerin is conventionally believed to be critical to the maintenance of CA-membrane permeability, medical devices (such as hemodialyzers, hemofilters, hemodiafilters, and the like) are conventionally packaged, shipped, and stored while impregnated with substantial amounts of glycerin. Elimination of the glycerin or replacement of the glycerin with any other substance is conventionally believed to cause an unacceptable degradation of permeability and, hence, membrane performance.

Unfortunately, according to conventional practice, the glycerin impregnant is at a concentration in the membrane that conventionally requires thorough rinsing to remove substantially all the glycerin before use. Having to perform such a pre-use rinse is cumbersome and inconvenient and consumes valuable time and resources in busy clinics.

Thus, there is a need for methods for manufacturing cellulose acetate membranes, and for manufacturing medical devices incorporating such membranes, that eliminate the need to maintain a substantial concentration of glycerin in the membranes from time of manufacture until time for their intended use.

There is also a need for methods for manufacturing cellulose acetate membranes, and for manufacturing medical devices incorporating such membranes, that contain an impregnant consisting substantially of water serving to maintain membrane permeability from time of manufacture until time of medical use of the membranes and devices.

There is also a need for cellulose acetate membranes, as well as medical devices comprising such membranes, that can be infused with a priming solution in preparation for medical use without having to discard the priming solution.

SUMMARY OF THE INVENTION

The foregoing needs are met by the present invention which provides methods for making cellulose acetate membranes, as well as for making medical devices incorporating such membranes. The present invention also provides cellulose acetate membranes, as well as medical devices incorporating such membranes, that contain an impregnant consisting substantially of water. The impregnant maintains the permeability of the membrane even during prolonged storage. Because the impregnant consists substantially of water, the membrane or device can be prepared for medical use by priming but without the need for discarding the priming solution.

According to one aspect of the present invention, a method is provided for making a cellulose acetate (CA) semipermeable membrane wherein a molten liquid is provided comprising CA, a solvent for the CA, and a non-solvent for the CA. The molten liquid is extruded to produce an extruded membrane, and the solvent and non-solvent are removed to produce a semipermeable membrane having a water permeability. Finally, the semipermeable membrane is impregnated with a liquid consisting substantially of water so as to render the membrane capable of being stored until time of use without undergoing a substantial loss in water permeability.

According to another aspect of the present invention, a CA semipermeable membrane is produced as described above. Before the membrane is impregnated with a liquid consisting substantially of water, the membrane is incorporated in a casing so as to produce a medical device. Afterward, the medical device is rinsed with the liquid consisting substantially of water to impregnate the membrane in the device with water and thus render the device capable of being stored until time of use without the membrane undergoing a substantial loss in water permeability.

According to yet another aspect of the present invention, a CA semipermeable membrane is produced as described above. In addition, before the membrane is impregnated with a liquid consisting substantially of water, the membrane is replasticized. A region of the replasticized membrane is exposed to a water-removing condition that renders, by removing water, the region capable of undergoing a bonding reaction with an adhesive. The replasticized membrane is assembled in a casing using an adhesive applied to at least a portion of the region, thereby producing a medical device. Finally, the replasticized membrane is rinsed with a liquid consisting substantially of water to remove the replasticizing agent from the membrane and to impregnate the membrane with water. Thus, the medical device is rendered capable of being stored without the membrane undergoing any substantial loss of water permeability.

According to yet other aspects of the present invention, semipermeable CA membranes, and medical devices incorporating such membranes, are provided that are made by methods as exemplified above.

A detailed discussion of the foregoing features and advantages of the present invention, as well as other features, is deferred to the following detailed description, which proceeds with reference to the accompanying drawing.

DETAILED DESCRIPTION

Figure 1:
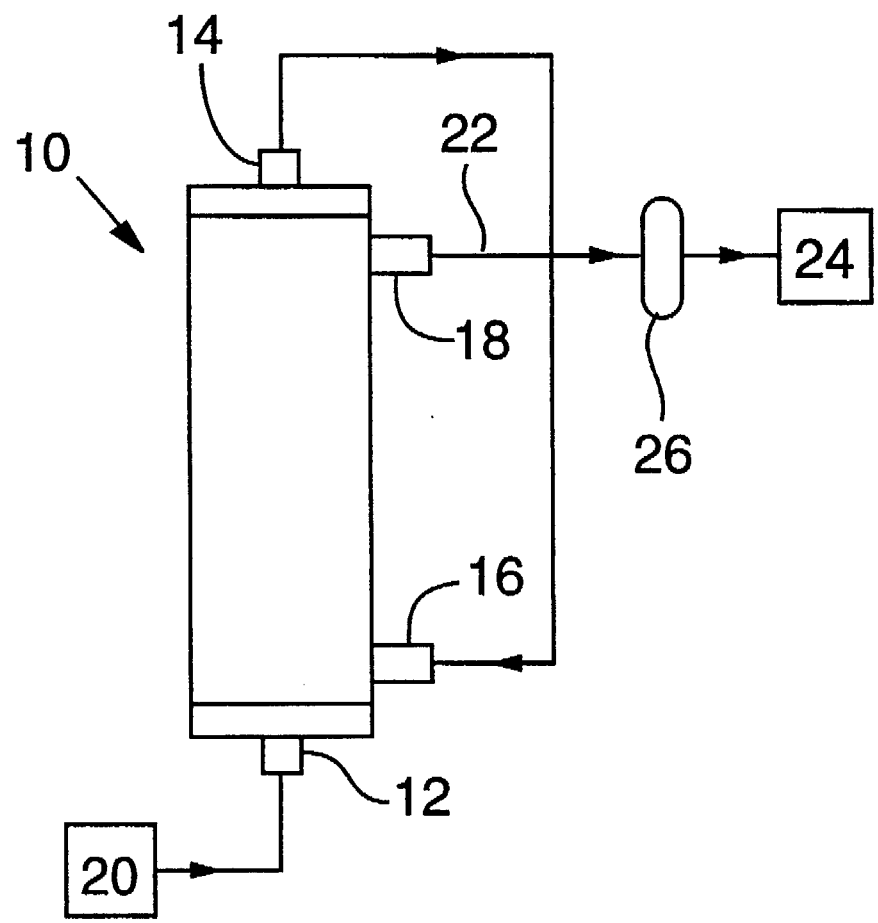
FIG. 1 is a schematic diagram of a preferred way of connecting a medical device, comprising CA hollow-fiber membranes, to a hydraulic circuit for the purpose of rinsing glycerin from the membranes.

The present invention provides semipermeable cellulose acetate (CA) membranes, including CA hollow-fiber membranes, that can be stored with a water impregnant until time for their intended use. In other words, the CA membranes can be stored, contrary to conventional practice, without an impregnant containing a substantial concentration of glycerin, so long as the membranes are not allowed to become desiccated (i.e, "dried" to such a degree that unacceptable changes to membrane permeability occur). Despite the absence of glycerin during storage, the CA membranes according to the present invention do not undergo any substantial degradation of performance. Such storage typically occurs after manufacture and incorporation of the membranes in medical devices (such as hemodialyzers, hemofilters, hemodiafilters, hemoconcentrators, or analogous devices), but can also occur before such incorporation, such as when the membrane is manufactured in a first location and transported to a second location where manufacture of the medical devices is performed.

The CA membranes according to the present invention also have any of various combinations of hydraulic (i.e., water) permeability and diffusive (i.e., solute) permeability. With respect to diffusive permeability, the membranes are permeable to solutes normally present in aqueous biological fluids (such as blood). Thus, the membranes provide suitable operating characteristics when used in, for example, medical separation processes or blood purification applications.

This invention also encompasses processes for making CA membranes and hollow fibers having the foregoing characteristics and benefits.

In addition to the foregoing properties, CA membranes made according to the present invention are resistant to thrombogenesis, and are non-toxic.

In accordance with a method for making CA membranes according to the present invention, cellulose acetate is liquified (i.e., melted) and combined with both a solvent for the CA and a non-solvent for the CA. The solvent and the non-solvent must be liquids at the melt temperature of the CA. Also, particularly if the membranes are intended for a medical or other use involving direct or indirect contact with living cells, the solvent and the non-solvent are preferably non-toxic and are not thrombogenic. The resulting molten mixture is mixed to homogeneity and extruded in a molten condition through an appropriate extrusion die.

As discussed below, the molten mixture can be extruded twice, once using a die suitable for making solid strands, then again using an appropriate die to produce the membrane. Extruding twice can yield superior control over the composition and characteristics of the finished membranes.

In the melt, molecules of the solvent and non-solvent constituents are homogeneously interspersed with CA molecules. During extrusion and subsequent cooling, the CA molecules undergo a degree of thermodynamic ordering of themselves relative to the solvent and non-solvent constituents. (This process is termed a "thermally-induced phase separation process," abbreviated "TIPS.") As a result, the CA molecules become associated with each other during extrusion to form a labyrinthine network.

After post-extrusion cooling of the membrane, solvent and non-solvent molecules are leached from the membrane by passing the membrane through heated water. Such leaching provides the membrane with an extensive and dense network of convoluted voids having an extremely fine mean pore size. These voids extend through the thickness dimension of the membrane and provide routes by which water and solutes can pass through the membrane during use. The molecules of the solvent and non-solvent, which originally occupied the voids, are substantially removed by passage of the membrane through heated water because, inter alia, these constituents do not become covalently bonded to the CA molecules.

For example, and not intended to be limiting, CA hollow fibers according to the present invention are made from a composition consisting essentially of a mixture of three compounds: (a) CA polymer which provides the structural aspect of the membrane; (b) glycerin (also termed "glycerol"), serving as a non-solvent for CA at ambient temperature; and (c) polyethylene glycol, serving as a solvent for CA at ambient temperature. A preferred mixture for making "high-flux" (i.e., high water permeability) CA hollow fibers suitable for hemodialysis use consists essentially of about 32 to about 40 percent (w/w) cellulose acetate, about 5 to about 10 percent (w/w) glycerin, and the balance polyethylene glycol having a molecular weight in a range of about 150 to about 600 daltons. The relative amounts of these three compounds in the melt can be changed to make CA hollow fibers having other permeability characteristics, as generally disclosed, for example, in U.S. Pat. No. 4,276,173 to Kell et al., incorporated herein by reference.

A preferred "double-extension" process for making CA membranes typically includes a "compounding" step in which the CA, the solvent, and the non-solvent are mixed to homogeneity at a temperature appropriate to melt cellulose acetate (about 165 to about 180° C.). The resulting first melt is extruded through a die to form solid strands. The strands are cooled and pelletized using conventional methods. The composition of the pellets is substantially the same as the composition of the first melt. Fabrication of CA membranes from the pellets formed from the first melt is performed by heating the pellets sufficiently to form a second "melt" which is extruded through an appropriate die.

CA membranes according to the present invention can also be extruded directly from the first melt, thereby avoiding the sequential production of two melts.

Preferred membrane configurations include sheets and hollow fibers. Extrusion dies and associated technology for producing these configurations are well known in the art. For example, for making a hollow-fiber membrane, an annular spinneret is used to extrude the melt. Forming hollow fibers in such a manner is termed "melt spinning" in the art.

The temperature of the melt during extrusion to form the membrane is a key parameter affecting the hydraulic permeability of the membrane. For example, with respect to CA hollow fibers, each one-degree Celsius increase in extrusion temperature causes a corresponding decrease in hydraulic permeability of the membrane by about 2 mL/min/mmHg/$m^2$. Thus, one way in which one can "customize" the hydraulic permeability of the CA membrane is by simply controlling the temperature.

It is important that the conditions under which the CA membrane is cooled upon exiting the extrusion die be maintained substantially constant to ensure uniform membrane characteristics over the length of the membrane produced by the die. These conditions include, but are not necessarily limited to, the temperature of the air used to cool the membrane, the velocity of air movement past the membrane, the longitudinal tension, if any, applied to the membrane as it exits the die, the rate at which the membrane is cooled relative to the longitudinal velocity of the membrane as it exits the die, and the humidity of the air used to cool the membrane. With respect to hollow-fiber CA membranes made according to the present invention, the longitudinal tension should be sufficient to longitudinally stretch the fiber by no greater than twenty percent.

After the membrane-forming extrusion step, the CA membrane is rapidly cooled, preferably in air. Subsequently, the membrane is passed through a heated-water bath to leach the solvent and the non-solvent from the membrane. The temperature of the heated-water bath is preferably about 80° to 95° C.

After passing through the heated-water bath, the membrane can be taken up in a wet condition on a reel or analogous appliance to await downstream manufacturing steps.

It is important that the CA membrane not be allowed to desiccate. Otherwise, irreversible damage to the membrane (e.g., excessive shrinkage of membrane pores) could result.

Until their intended use, a CA membrane must contain a substance that substantially maintains the intended permeability of the membrane. According to the prior art, this substance must be or include a substantial concentration of glycerin. We have found that CA-membrane permeability can be maintained using water and substantially no glycerin, even for extended storage periods.

However, certain manufacturing steps (such as application of adhesives or "potting" substances to the membrane) applicable to incorporation of the membrane into certain medical devices (e.g., hollow-fiber devices such as hemodialyzers) require that selected portions of the CA membrane not contain any substantial amounts of water during execution of the step. In such an instance, it is possible to temporarily impregnate the membrane with a hydrophilic substance that maintains membrane permeability even when a sufficient amount of water is removed from the membrane to facilitate, e.g., proper adhesion. Such temporary impregnation is termed "replasticization" of the membrane.

By way of example, wet CA membranes can be replasticized by immersion in or application of an aqueous solution of about 30 to 40% (w/w) glycerin at about 25° C., wherein the glycerin serves as the "replasticization agent." The replasticized membranes are subsequently exposed to a condition suitable for removing water, but not the replasticization agent, from the membranes. Preferably, the water-removal condition constitutes exposure of the membrane to air heated to about 70° to 80° C., after which the equilibrium concentration of glycerin in the CA membrane is about 45 to 50% (w/w) and water about 15 to 18% (w/w).

A replasticized membrane can be wound on a drum, reel, or analogous appliance for temporary storage until time for use in making medical devices.

Continuing with a representative method for making hollow-fiber devices, as well-known in the art, replasticized CA hollow fibers are normally arrayed into discrete bundle (s) each containing multiple (e.g., a large number of) hollow fibers arrayed substantially parallel to each other. The bundles are trimmed to a length sufficient for insertion of the bundle into a rigid tubular jacket or sheath. Subsequent "potting" of each bundle end in the jacket is normally performed using a polyurethane or other suitable potting agent. To facilitate adhesion of the potting agent to all the individual fibers in each bundle end, water is removed from at least the bundle ends as generally described above. (Reference is made, for example, to U.S. Pat. No. 5,182,868, incorporated herein by reference, specifically disclosing one manner in which "bundle-end drying" can be performed.) A header cap is then attached to each end of the jacket to complete assembly of the device.

Before packaging the medical devices, substantially all glycerin is removed from the membranes by a water-rinsing step, whether the CA membranes had been replasticized or not. The water-rinsing step is preferably performed using subatmospheric pressure to facilitate satisfactory withdrawal of glycerin from the membrane pores.

FIG. 1 schematically illustrates a preferred method for removing glycerin from a medical device 10 incorporating membranes according to the present invention. The medical device 10 is shown in a typical configuration for a hemodialyzer, hemodiafilter, or the like. The FIG.-1 method is particularly suitable for automation. Referring to FIG. 1, the device 10 is shown having a first "blood" port 12, a second "blood" port 14, a first "dialysate" port 16, and a second "dialysate" port 18. The first "blood" port 12 is connected to a water (preferably deionized and/or distilled) supply 20; the second "blood" port 14 is connected to the first "dialysate" port 16, and the second "dialysate" port 18 is connected by a conduit 22 to an aspirator 24 such as a venturi or "vacuum" aspirator. The aspirator 24 controllably applies a subatmospheric pressure to the device 10 so as to facilitate not only rinsing of the major surfaces of the membranes but also passage of water through the membrane pores. A valve 26 can be interposed in the conduit 22 to control the timing of application of subatmospheric pressure to the device 10.

For removal of substantially all glycerin from CA membranes, application of subatmospheric pressure while rinsing with water is particularly advantageous because it facilitates removal of glycerin from the membrane pores as well as from membrane surfaces. The subatmospheric pressure creates a "transmembrane pressure" across the membrane thickness dimension serving to create a net flow of water through the membrane pores. The flow of water through the pores dislodges glycerin molecules from the pores. Thus, rinsing of glycerin using subatmospheric pressure is indicated even if the membranes have not been replasticized. This is because the rinsing as described above can remove glycerin remaining in the membrane pores after the heated-water leaching step.

Water from the supply 20 is preferably pyrogen-free and, for most hollow-fiber medical devices, is provided at a pressure of 5 psig, a flow rate of 1 L/min, and a temperature of 60°-75° F. The water passes first through the lumina of the CA hollow fibers and then co-currently through a compartment of the device in which the water can bathe the exterior surfaces of the fibers.

According to the water-rinsing scheme shown in FIG. 1, and applying the pressure and flow rate parameters set forth above, an initial concentration of glycerin in the device of about 24000 ppm can be reduced to about 90 ppm within three minutes of water rinsing.

Rinsing of absolutely all glycerin from the CA membranes is normally not possible within normal manufacturing constraints. But, absolute removal of glycerin is not required to render the device medically safe. Thus, as used herein, a removal of "substantially all" glycerin from the membranes is the attainment of a glycerin concentration in the rinse water leaving the device of about 300 ppm or less, which is medically acceptable. In various tests, we have attained glycerin concentrations, using the foregoing procedures, of about 20 ppm.

Rinsing of glycerin from the CA membranes can be performed at any of various stages of manufacturing the medical device, depending upon whether or not the membranes needed to be replasticized during manufacture of the device and on practical considerations involving the prevailing manufacturing conditions and equipment. With replasticized membranes, removal of glycerin is typically performed at some point in manufacture after completion of all adhesion step(s) requiring replasticized membranes. Most conveniently, the glycerin-rinsing step is performed after completion of device manufacture but before packaging of the device.

As discussed above, prior-art processes for making CA membranes require that the membranes be kept impregnated with a substantial amount of glycerin in order to maintain the desired membrane water permeability and solute clearance until time of use. We have found, in contrast, that glycerin impregnation is not required in order to maintain membrane permeability, even with membranes that are stored for extended periods of time. Rather, keeping the CA membranes impregnated with water, according to the present invention, during storage does not cause any significant degradation of water permeability. Solute clearances of CA membranes made according to the present invention, compared to solute clearances of otherwise identical CA membranes made by conventional methods, range from unchanged to a decline of about 5 to 10 percent, which is acceptable for current medical uses. For CA membranes intended for use in hemoconcentrators, any decrease in solute clearance is immaterial because hemoconcentrators are only intended for use in removing water, not solutes, from biological fluids such as blood.

A key benefit of CA membranes made according to the present invention (as well as medical devices incorporating such membranes) is that the membranes can be primed for use without having to pre-rinse and without having to discard the priming solution. The devices simply can be primed and used immediately. Conventional CA membranes (as well as medical devices incorporating such membranes) require pre-rinsing. Thus, the rinsing or priming solution, which contains a large concentration of glycerin removed from the membranes, must be discarded. Being able to clinically use a CA membrane-containing device without pre-rinsing and/or discarding the priming solution is particularly beneficial in saving time in busy clinics. Also, such membranes and associated devices do not require additional equipment dedicated to pre-rinsing and purging of glycerin.

While the present invention has been described in connection with preferred embodiments, it will be understood that it is not limited to these embodiments. On contrary, the invention is intended to cover all alternatives, modifications, and equivalents as may be included within the spirit and scope of the invention as defined by the appended claims.

What is claimed is:

1. A method for making a cellulose acetate semipermeable membrane, comprising the steps:
    (a) providing a molten liquid comprising cellulose acetate, a solvent for cellulose acetate, and a non-solvent for cellulose acetate;
    (b) extruding the molten liquid to produce an extruded membrane;
    (c) removing the solvent and the non-solvent from the extruded membrane to produce a semipermeable membrane having a water permeability; and
    (d) impregnating the semipermeable membrane with a liquid consisting essentially of water so as to render the semipermeable capable of being stored until time of use while retaining the water permeability of the semipermeable membrane.

2. A method for making a medical device comprising a cellulose acetate membrane, the method comprising the steps:
    (a) providing a molten liquid comprising a substantially uniform mixture of cellulose acetate, a solvent for cellulose acetate, and a non-solvent for cellulose acetate;
    (b) extruding the molten liquid to produce an extruded membrane;
    (c) removing the solvent and the non-solvent from the extruded membrane to produce a semipermeable membrane having a water permeability;
    (d) incorporating the semipermeable membrane in a casing so as to produce a medical device; and
    (e) rinsing the medical device with a liquid consisting essentially of water to impregnate the semipermeable membrane in the device with water and thus render the device capable of being stored until time of use while retaining the water permeability of the semipermeable membrane.

3. A method according to claim 2 wherein the solvent is polyethylene glycol and the non-solvent is glycerin.

4. A method according to claim 2 wherein, in step (e), the device is rinsed with the liquid so as to apply a transmembrane pressure to the semipermeable membrane.

5. A method for making a medical device comprising a cellulose acetate semipermeable membrane, the method comprising the steps:
    (a) providing a molten liquid comprising cellulose acetate, a solvent for cellulose acetate, and a non-solvent for cellulose acetate;
    (b) extruding the molten liquid to produce an extruded membrane;
    (c) removing the solvent and the non-solvent from the extruded membrane to produce a semipermeable membrane having a water permeability;
    (d) replasticizing the semipermeable membrane;
    (e) exposing a region of the replasticized membrane to a water-removing condition so as to render the region capable of undergoing a bonding reaction with an adhesive;
    (f) assembling the replasticized membrane in a casing using an adhesive applied to at least a portion of the region so as to produce a medical device; and
    (g) rinsing the replasticized membrane with a liquid consisting substantially of water to remove the replasticizing agent from the membrane and to impregnate the membrane with water so as to enable the medical device to be stored while retaining the water permeability of the semipermeable membrane.

6. A method according to claim 5 wherein the solvent is polyethylene glycol and the non-solvent is glycerin.

7. A method according to claim 5 wherein, in step (d), the membrane is replasticized using a replasticizing liquid comprising glycerin.

8. A method according to claim 5 wherein, in step (g), the device is rinsed with the liquid so as to apply a transmembrane pressure to the semipermeable membrane.

9. A method for making a medical device comprising a cellulose acetate semipermeable membrane, the method comprising the steps:
    (a) providing a molten liquid comprising a substantially uniform mixture of cellulose acetate, a solvent for cellulose acetate, and a non-solvent for cellulose acetate;
    (b) extruding the molten liquid to produce an extruded membrane;
    (c) removing the solvent and the non-solvent from the extruded membrane to produce a semipermeable membrane having a water permeability;
    (d) replasticizing the semipermeable membrane;
    (e) incorporating the semipermeable membrane in a casing so as to produce a medical device; and
    (f) rinsing the medical device with a liquid consisting essentially of water to impregnate the semipermeable membrane in the device with water and thus renders the device capable of being stored until time of use while retaining the water permeability of the semipermeable membrane.

10. The method of claim 9, wherein the solvent is polyethylene glycol and the non-solvent is glycerin.

* * * * *